(12) United States Patent
Abbasi

(10) Patent No.: US 10,966,758 B2
(45) Date of Patent: Apr. 6, 2021

(54) REINFORCEMENT CAPS FOR SPINAL SUPPORT SYSTEMS

(71) Applicant: Advance Research System, LLC, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 32 days.

(21) Appl. No.: 15/970,429

(22) Filed: May 3, 2018

(65) Prior Publication Data

US 2018/0317973 A1 Nov. 8, 2018

Related U.S. Application Data

(60) Provisional application No. 62/500,719, filed on May 3, 2017, provisional application No. 62/500,820, filed on May 3, 2017.

(51) Int. Cl.
*A61B 17/70* (2006.01)
*A61B 17/86* (2006.01)
*A61B 17/56* (2006.01)

(52) U.S. Cl.
CPC ...... *A61B 17/7032* (2013.01); *A61B 17/7034* (2013.01); *A61B 17/7037* (2013.01);
(Continued)

(58) Field of Classification Search
CPC ............................................ A61B 17/70–7046
See application file for complete search history.

(56) References Cited

U.S. PATENT DOCUMENTS 5,261,912 A * 11/1993 Frigg ................. A61B 17/7002
606/302
5,520,690 A * 5/1996 Errico ................. A61B 17/7037
606/287
(Continued)

FOREIGN PATENT DOCUMENTS

KR  10-2010-0119303    11/2010
WO  WO 2010/028287    3/2010
(Continued)

OTHER PUBLICATIONS

International Search Report for Application No. PCT/US2018/030928 dated Sep. 27, 2018 (3 pages).

*Primary Examiner* — Eduardo C Robert
*Assistant Examiner* — Steven J Cotroneo
(74) *Attorney, Agent, or Firm* — Christensen, Fonder, Dardi & Herbert PLLC

(57) ABSTRACT

A reinforcement cap for use with pedicle screws and rod receptacles ("tulips") in spinal support systems. The unitary reinforcement cap engages both the internal and the external surfaces of the wall segments of the rod receptacle. In some embodiments, both the internal and the external surfaces are threadably engaged. By doubling the number of threads that are engaged, additional strength and structural integrity are realized over conventional set screw arrangements. Also, because of the unitary construction, wherein an internal set screw portion and an external skirt portion are integral to the reinforcement cap, lateral movement between the set screw portion and the skirt portion is limited. In some embodiments, the threads are of a canted cantilever construction, wherein the interfaces of threadably engaged components are tailored to generate reaction force vectors that mitigate slippage at the threaded interfaces.

18 Claims, 9 Drawing Sheets

(52) U.S. Cl.
CPC ...... *A61B 17/7049* (2013.01); *A61B 17/8605* (2013.01); *A61B 17/7002* (2013.01); *A61B 17/7074* (2013.01); *A61B 2017/564* (2013.01)

(56) References Cited

U.S. PATENT DOCUMENTS

| | | | |
|---|---|---|---|
| 5,669,911 A * | 9/1997 | Errico | A61B 17/7034 606/264 |
| 5,672,176 A * | 9/1997 | Biedermann | A61B 17/7037 606/271 |
| 5,782,833 A | 7/1998 | Haider | |
| 5,882,350 A * | 3/1999 | Ralph | A61B 17/7037 606/278 |
| 5,964,760 A | 10/1999 | Richelsoph | |
| 6,074,391 A | 6/2000 | Metz-Stavenhagen et al. | |
| 6,248,105 B1 * | 6/2001 | Schlapfer | A61B 17/7032 606/266 |
| 6,296,642 B1 | 10/2001 | Morrison et al. | |
| 6,440,137 B1 * | 8/2002 | Horvath | A61B 17/7032 606/302 |
| 6,520,963 B1 * | 2/2003 | McKinley | A61B 17/7032 606/266 |
| 6,585,737 B1 * | 7/2003 | Baccelli | A61B 17/7032 606/273 |
| 6,835,196 B2 | 12/2004 | Biedermann et al. | |
| 6,843,791 B2 * | 1/2005 | Serhan | A61B 17/7037 606/272 |
| 7,156,850 B2 | 1/2007 | Kim | |
| 7,291,151 B2 | 11/2007 | Alvarez | |
| 7,445,627 B2 * | 11/2008 | Hawkes | A61B 17/7032 606/266 |
| 7,896,902 B2 * | 3/2011 | Jeon | A61B 17/7037 606/246 |
| RE42,545 E | 7/2011 | Ralph et al. | |
| 8,083,776 B2 | 12/2011 | Alvarez | |
| 8,257,402 B2 * | 9/2012 | Jackson | A61B 17/7032 606/273 |
| 8,273,109 B2 * | 9/2012 | Jackson | A61B 17/7032 606/273 |
| 8,337,532 B1 | 12/2012 | McLean et al. | |
| 8,702,758 B2 | 4/2014 | Wang et al. | |
| 8,747,405 B2 | 6/2014 | Belliard | |
| 8,852,241 B2 | 10/2014 | Datta | |
| 8,870,928 B2 * | 10/2014 | Jackson | A61B 17/7032 606/273 |
| 9,023,087 B2 | 5/2015 | Frankel et al. | |
| 9,277,950 B2 | 3/2016 | Buttermann | |
| 9,427,260 B2 * | 8/2016 | Juchno | A61B 17/704 |
| 9,451,994 B1 | 9/2016 | Whipple et al. | |
| 9,510,867 B2 * | 12/2016 | Garamszegi | A61B 17/7032 |
| 10,149,702 B2 * | 12/2018 | Ewer | A61B 17/7038 |
| 2002/0082602 A1 | 6/2002 | Biedermann et al. | |
| 2003/0125741 A1 | 7/2003 | Biedermann et al. | |
| 2004/0249380 A1 | 12/2004 | Glascott | |
| 2006/0079895 A1 * | 4/2006 | McLeer | A61B 17/863 606/279 |
| 2007/0055238 A1 | 3/2007 | Biedermann et al. | |
| 2008/0287998 A1 | 11/2008 | Doubler et al. | |
| 2010/0094353 A1 | 4/2010 | Shim et al. | |
| 2010/0160981 A1 | 6/2010 | Butler et al. | |
| 2011/0190821 A1 | 8/2011 | Chin et al. | |
| 2012/0130436 A1 | 5/2012 | Haskins et al. | |
| 2012/0215263 A1 | 8/2012 | Lee | |
| 2012/0271365 A1 | 10/2012 | Daubs et al. | |
| 2013/0345755 A1 | 12/2013 | Prajapati et al. | |
| 2014/0094849 A1 | 4/2014 | Spratt et al. | |
| 2014/0121703 A1 | 5/2014 | Jackson et al. | |
| 2014/0135839 A1 | 5/2014 | Frankel et al. | |
| 2014/0135854 A1 | 5/2014 | Dec et al. | |
| 2014/0148858 A1 | 5/2014 | Dant et al. | |
| 2014/0316475 A1 | 10/2014 | Parikh et al. | |
| 2016/0242817 A1 | 8/2016 | Abbasi | |
| 2018/0228518 A1 | 8/2018 | Carruth et al. | |

FOREIGN PATENT DOCUMENTS

| | | |
|---|---|---|
| WO | WO 2010/037098 | 4/2010 |
| WO | WO 2014/052117 | 4/2014 |
| WO | WO 2014/138736 | 9/2014 |

* cited by examiner

REINFORCEMENT CAPS FOR SPINAL SUPPORT SYSTEMS

RELATED APPLICATION

This patent application claims the benefit of U.S. Provisional Patent Application No. 62/500,719, filed on May 3, 2017, and U.S. Provisional Patent Application No. 62/500,820, also filed May 3, 2017, the disclosures of which are hereby incorporated by reference in their entirety.

FIELD OF THE DISCLOSURE

The present disclosure relates to spinal support systems and more particularly to reinforcement of spinal support systems and methods.

BACKGROUND OF THE DISCLOSURE

Spinal support systems utilizing pedicle screws and spinal rods disposed in rod receptacles or "tulips" have been used to support spinal vertebrae. The purpose of such systems vary. In some applications, the spinal support system is used in spinal fusion therapy to hold adjacent vertebrae stationary with respect to each other, enabling bone growth tissue to form. In some applications, the rods are placed in tension to correct spinal maladies (e.g., scoliosis).

The rod receptacles typically define diametrically oppose slots, with the spinal rod extending through the slots. The formation of the slots further define opposed wall segments that extend proximally on lateral sides of the spinal rod. The spinal rod is typically held within the slots with a set screw that threadably engages the wall segments.

Over time, creep stresses may cause the wall segments to deflect radially outward and away from the set screw, with an accompanying decrease the clamping force of the set screw against the spinal rod. This can cause loosening of the assembly and slippage of the resident spinal rod within the spinal rod receptacle. In some instances, torque requirements, particularly where the spinal rods are subject to high tension forces, can cause the set screw to slip within the spinal rod receptacle during implantation. A system that remedies these shortcomings of conventional spinal support systems would be welcomed.

SUMMARY OF THE DISCLOSURE

In various embodiments of the disclosure, a spinal support system is disclosed where a unitary reinforcement cap threadably engages both the internal and the external surfaces of the wall segments of the rod receptacle. By doubling the number of threads that are engaged, additional strength and structural integrity are realized over standard set screw arrangements. Also, because of the unitary construction, wherein an internal set screw portion and an external skirt portion are integral to the reinforcement cap, lateral movement between the set screw portion and the skirt portion is limited.

In some embodiments, the unitary reinforcement cap does not threadably engage the external surface, but instead slidingly engages the external surface to provide support to the rod receptacle. Accordingly, such embodiments do not require the presence of threads on the external surface of the rod receptacle, and can be configured for a retrofit of conventional rod receptacles.

In some embodiments, the threads are of a canted cantilever construction, wherein the interfaces of threadably engaged components are tailored to generate reaction force vectors that prevent slippage at the interfaces.

Structurally, a reinforcement cap is disclosed for a spinal support system, comprising: a platform portion including a distal face and a proximal face separated by a perimeter portion; a skirt portion that extends from the distal face of the platform portion, the skirt portion including an interior surface, at least a portion of the interior surface including interior threads formed thereon; and a set screw portion that extends from the distal face of the platform portion, the set screw portion being surrounded by the skirt portion and including an exterior surface that faces radially outward, at least a portion of the exterior surface including exterior threads formed thereon, the set screw portion defining a rotation axis, the set screw portion and the skirt portion being concentric about the rotation axis to define an annular gap between the exterior threads of the set screw portion and the interior threads of the skirt portion. The skirt portion may include an exterior surface that is tangential with the perimeter portion. In some embodiments, the set screw portion extends distally beyond the skirt portion. The skirt portion may include an exterior surface that defines a plurality of flats, each of the plurality of flats being parallel to the rotation axis.

In some embodiments, the exterior threads of the set screw portion define a canted cantilever profile. Likewise, in some embodiments, the interior threads of the skirt portion define a canted cantilever profile. The canted cantilever profile of the set screw portion may slope in a distal direction and toward the rotation axis. The canted cantilever profile of the set screw portion may slope in a distal direction and away from the rotation axis.

In some embodiments, the platform portion defines a socket accessible from the proximal face, the socket being concentric with and extending along the rotation axis. The platform portion may also define a tapped center hole accessible from the proximal face, the tapped center hole being concentric with and extending along the rotation axis, the socket extending distally from the tapped center hole. The reinforcement cap may further define a center passage concentric with the rotation axis and extending from the socket through a distal end of the set screw portion.

In various embodiments of the disclosure, a spinal support system comprises the reinforcement cap as described above; and a spinal rod receptacle having a side wall that includes an interior surface and an exterior surface, the side wall defining a pair of diametrically opposed slots that extend axially along the side wall and are open at a proximal end of the spinal rod receptacle, the interior surface of the spinal rod receptacle defining interior threads, the exterior surface of the spinal rod receptacle defining first exterior threads, wherein the interior threads of the spinal rod receptacle are configured to mate with the exterior threads of the set screw portion of the reinforcement cap, and the exterior threads of the spinal rod receptacle are configured to mate with the interior threads of the skirt portion of the reinforcement cap. In various embodiments, a spinal rod is configured for insertion into the diametrically opposed slots. A pedicle screw may be disposed within the spinal rod receptacle, a shaft of the pedicle screw extending distally from the spinal rod receptacle.

In various embodiments of the disclosure, a method for securing a spinal support rod to a spinal rod receptacle is disclosed, comprising: (a) disposing a spinal support rod through diametrically opposed slots of a spinal rod receptacle; (b) threadably engaging interior threads of a skirt portion of a reinforcement cap with exterior threads of the spinal rod receptacle; (c) simultaneously with step (b), threadably engaging exterior threads of a set screw portion of the reinforcement cap with interior threads of the spinal rod receptacle; and (d) tightening the reinforcement cap against the spinal support rod. In some embodiments, step (d) includes driving the reinforcement cap with a tool that mates with a socket formed on the reinforcement cap. In some embodiments, step (d) includes driving the reinforcement cap with a tool that engages flats formed on the skirt portion of the reinforcement cap.

DETAILED DESCRIPTION OF THE FIGURES

Figure 1:
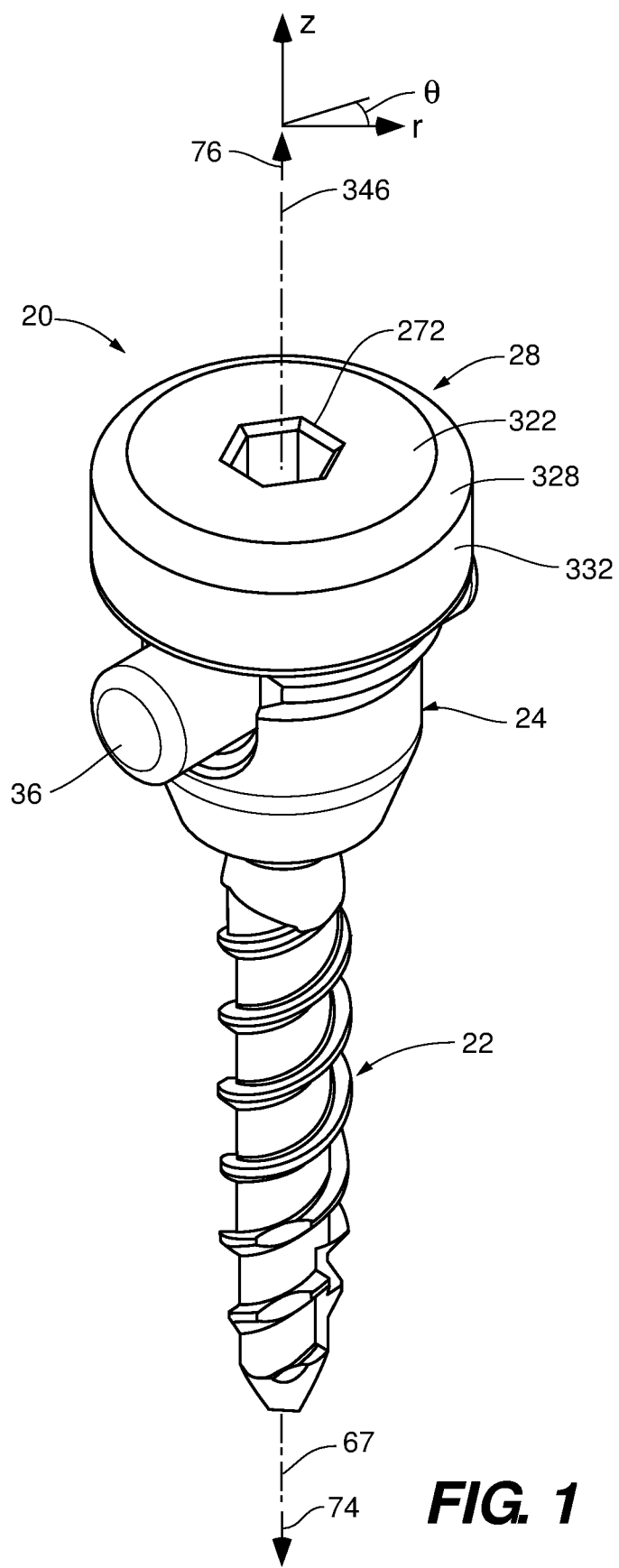
FIG. 1 is an upper perspective view of a spinal support system according to an embodiment of the disclosure.
Figure 2:
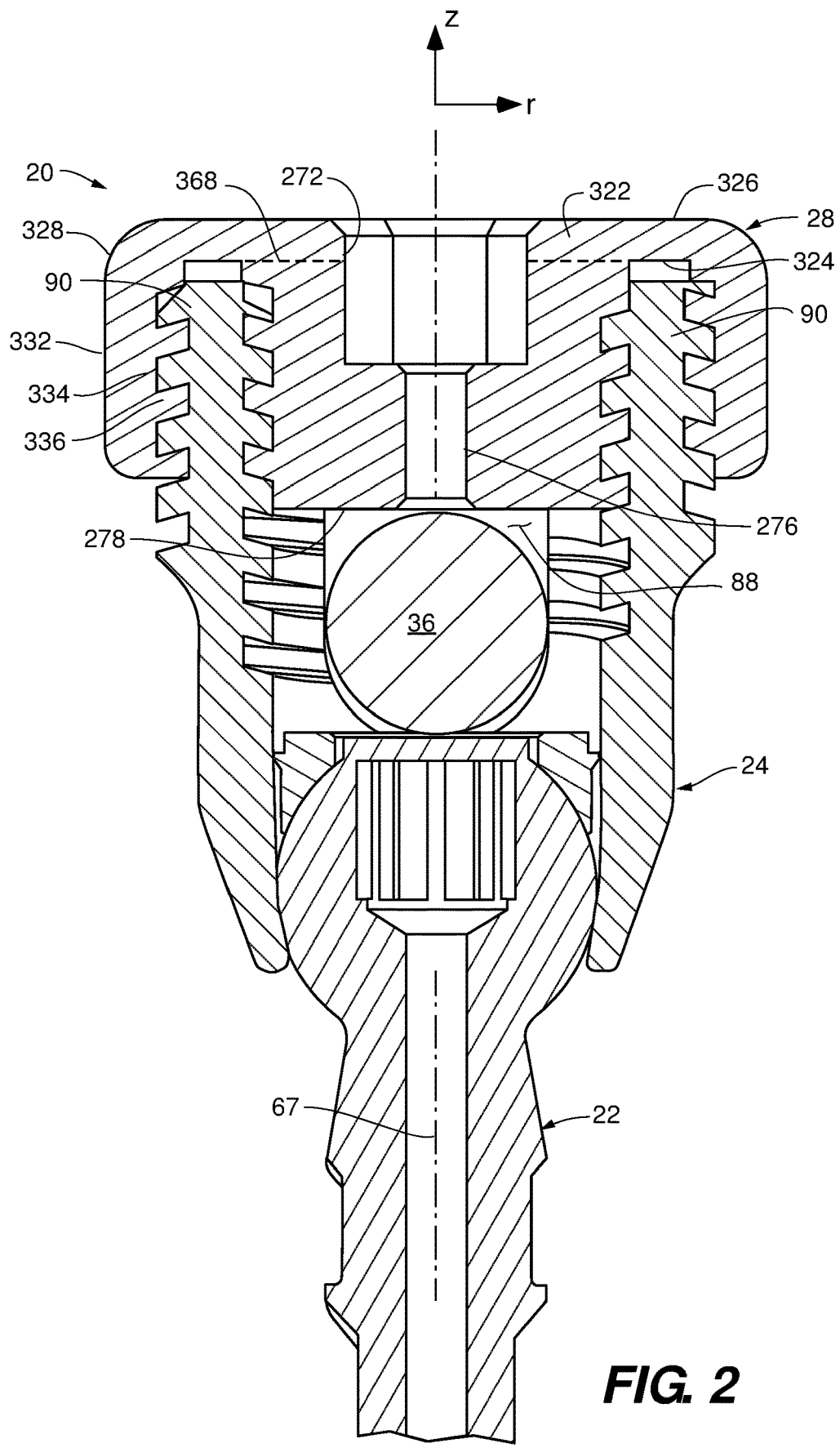
FIG. 2 is a partial sectional view of the spinal support system of FIG. 1 according to an embodiment of the disclosure.
Figure 3:
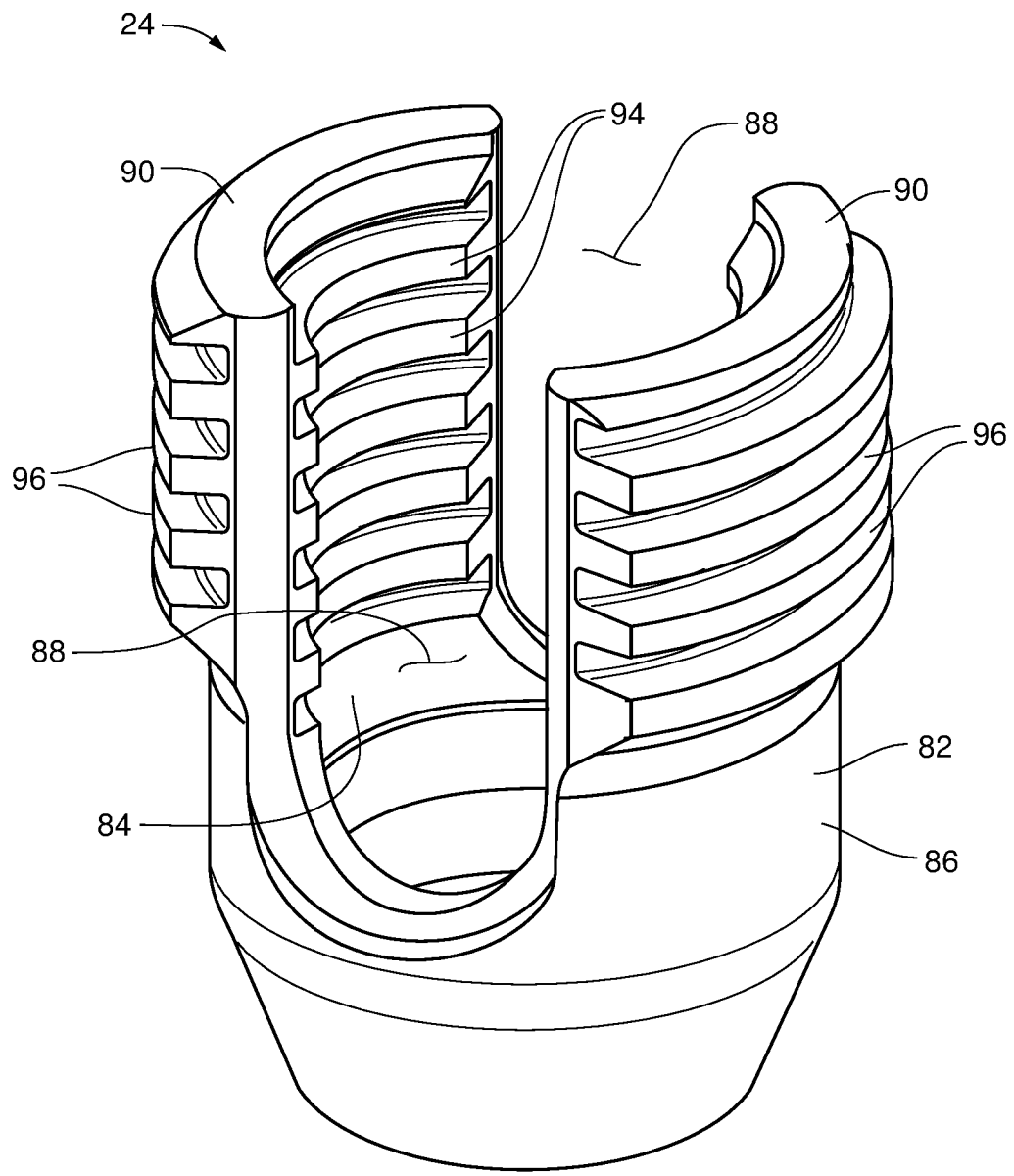
FIG. 3 is an upper perspective view of a spinal rod receptacle in isolation according to an embodiment of the disclosure.

Referring to FIGS. 1 through 3, a spinal support system 20 is depicted according to an embodiment of the disclosure. The spinal support system 20 includes a pedicle screw 22, a spinal rod receptacle 24, a reinforcement cap 28, and a spinal support rod 36 (FIG. 1). The spinal rod receptacle 24 is configured to receive the spinal support rod 36. In the depicted embodiment, the spinal support rod 36 is retained within the spinal rod receptacle 24 with the cap 28. The pedicle screw 22, spinal rod receptacle 24, and reinforcement cap 28 are aligned along a center axis 67.

The spinal rod receptacle 24 includes a side wall 82 having an interior surface 84 and an exterior surface 86 (FIG. 3). A pair of diametrically oppose slots 88 are defined on the side wall 82, the slots 88 extending axially along the side wall 82 and being open at a proximal end 92 of the spinal rod receptacle 24. By formation of the diametrically opposed slots 88, the side wall 82 defines diametrically opposed wall segments 90 on opposing sides of the diametrically opposed slots 88. The interior surface 84 extends axially along the side wall 82 and includes interior threads 94 formed thereon. The exterior surface 86 also extends axially and includes exterior threads 96 formed thereon.

Figure 4:
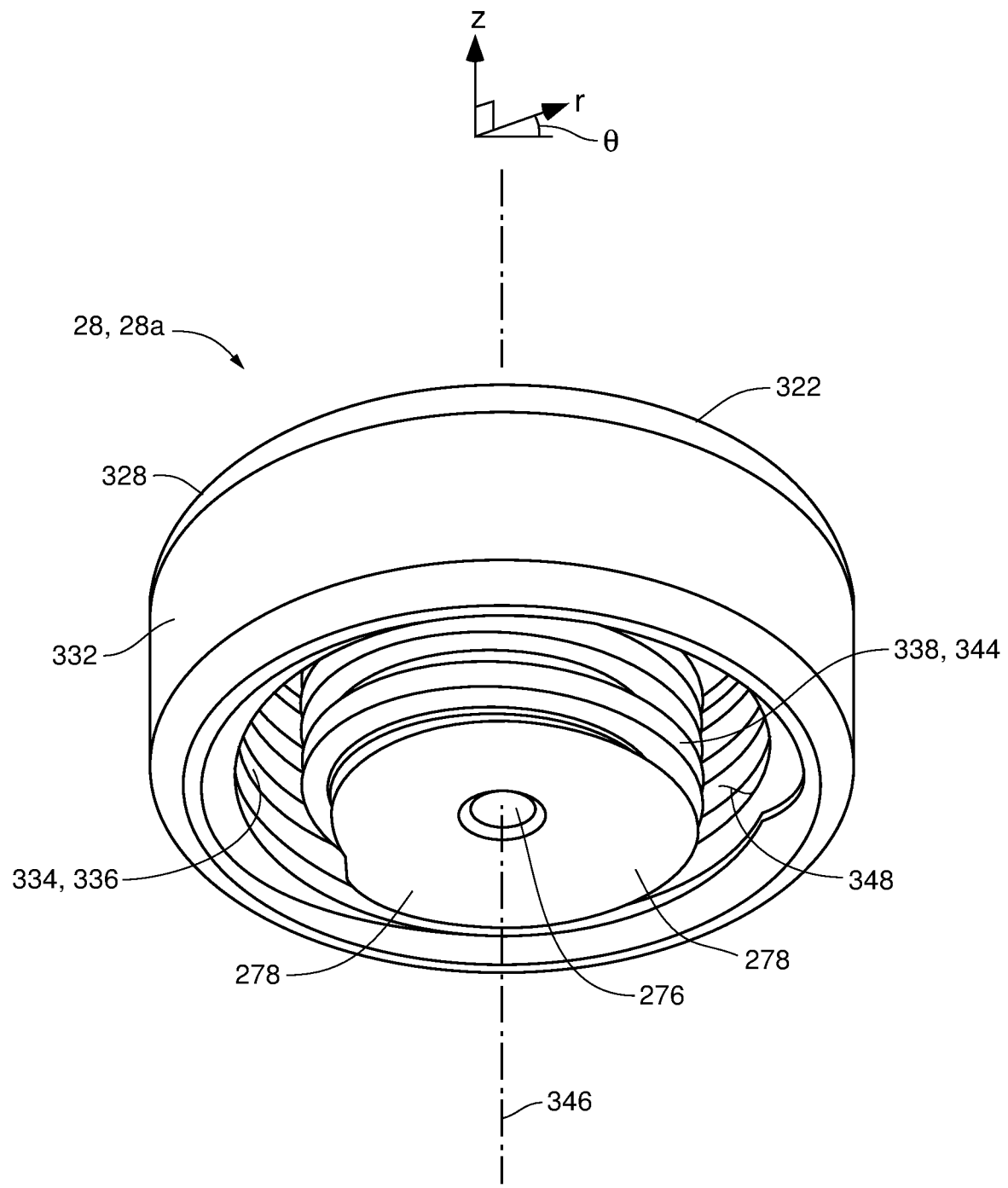
FIG. 4 is a lower perspective view of a reinforcement cap according to an embodiment of the disclosure.
Figure 5:
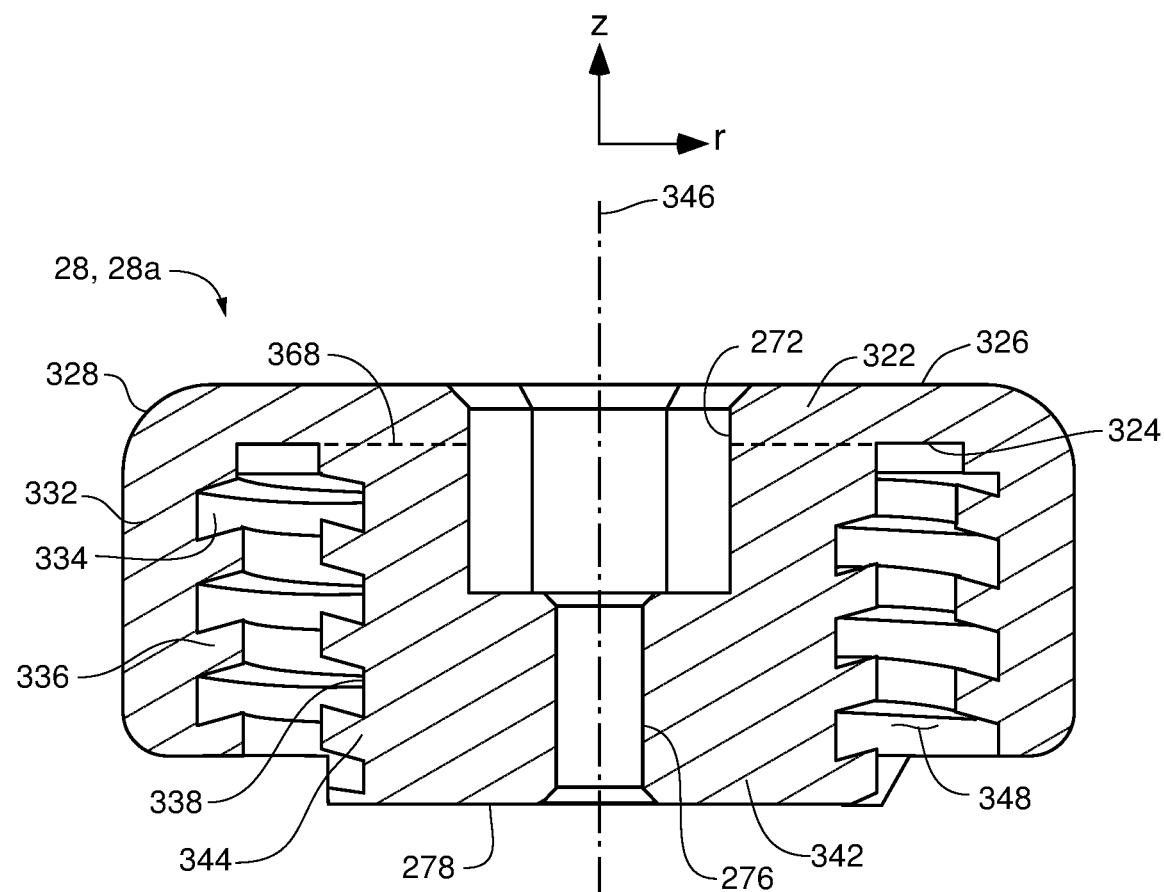
FIG. 5 is a sectional view of the reinforcement cap of FIG. 4 according to an embodiment of the disclosure.

Referring to FIGS. 4 and 5, a reinforcement cap 28a is depicted according to an embodiment of the disclosure. Herein, various reinforcement caps are presented and referred to collectively and generically by reference character 28, and specifically by the reference character 28 followed by a letter suffix (e.g., reinforcement cap 28a). The reinforcement cap 28a includes a platform portion 322 including a distal face 324 and a proximal face 326 separated by a perimeter portion 328 (FIGS. 2, 4, and 5). A skirt portion 332 extends from the distal face 324 of the platform portion 322 portion, the skirt portion 332 including an interior surface 334, at least a portion of which includes interior threads 336 formed thereon. A set screw portion 342 extends from the distal face 324 of the platform portion 322, the set screw portion 342 being surrounded by the skirt portion 332 and including an exterior surface 338 that faces radially outward. At least a portion of the exterior surface 338 includes exterior threads 344 formed thereon. The set screw portion 342 defines a rotation axis 346 about which the set screw portion 342 and the skirt portion 332 are concentric. An annular gap 348 is defined between the exterior threads 344 of the set screw portion 342 and the interior threads 336 of the skirt portion 332.

The reinforcement cap 28a may define a socket 272 accessible from the proximal face 326 of the cap 28a. In the depicted embodiment, the socket 272 is hexagonal, but other geometries, such as a square, rectangle, octagon, cross, or star pattern may be utilized. In some embodiments, a center passage 276 extends from the socket 272 through a distal end 278 of the set screw portion 342. Herein, "proximal" refers to a direction 76 that is toward a surgeon during operation or implantation and away from a bone or patient (FIG. 1). "Distal" refers to a direction 74 that is away from the surgeon during operation or implantation and toward the bone or patient to which the extensible spinal support system 20 is mounted (i.e., a direction opposite the distal direction).

Figure 6:
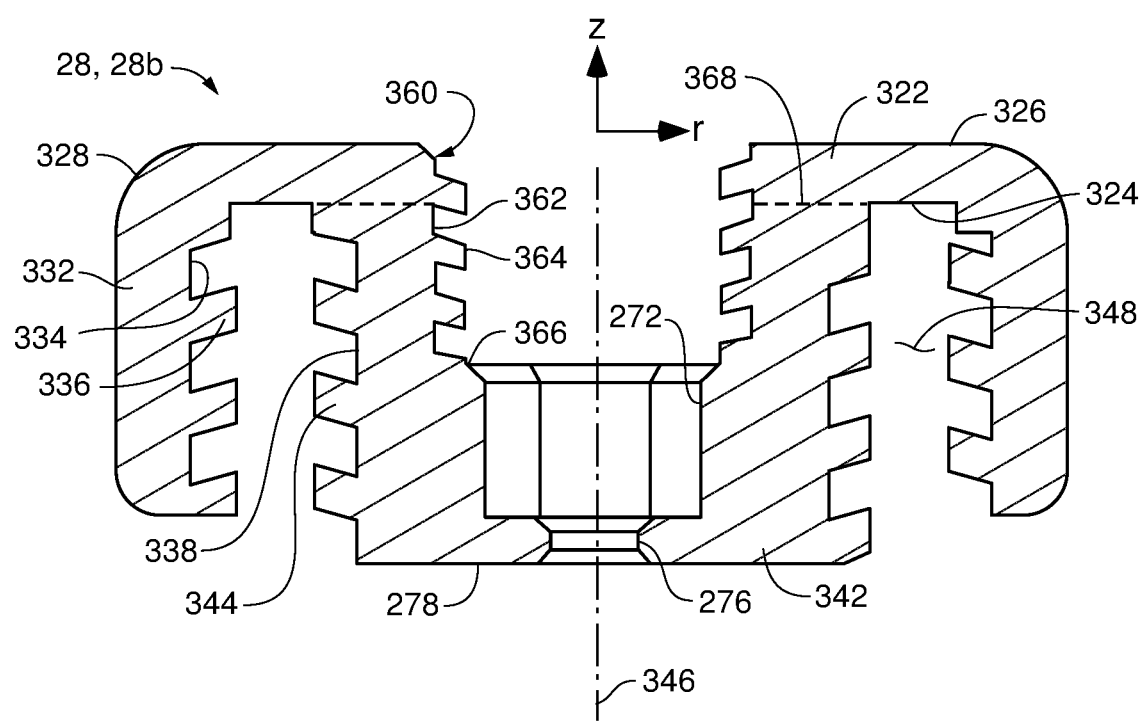
FIG. 6 is a sectional view of a reinforcement cap having a tapped center hole according to an embodiment of the disclosure.

Referring to FIG. 6, a reinforcement cap 28b modified to define a tapped center hole 360 is depicted according to an embodiment of the disclosure. The reinforcement cap 28b includes many of the same components and attributes as the reinforcement cap 28a, which are indicated with same-numbered numerical characters. The tapped center hole 360 is characterized as having an inner wall 362 on which threads 364 are formed, and a bottom surface 366. The socket 272 extends distally from the bottom surface 366.

Figure 7:
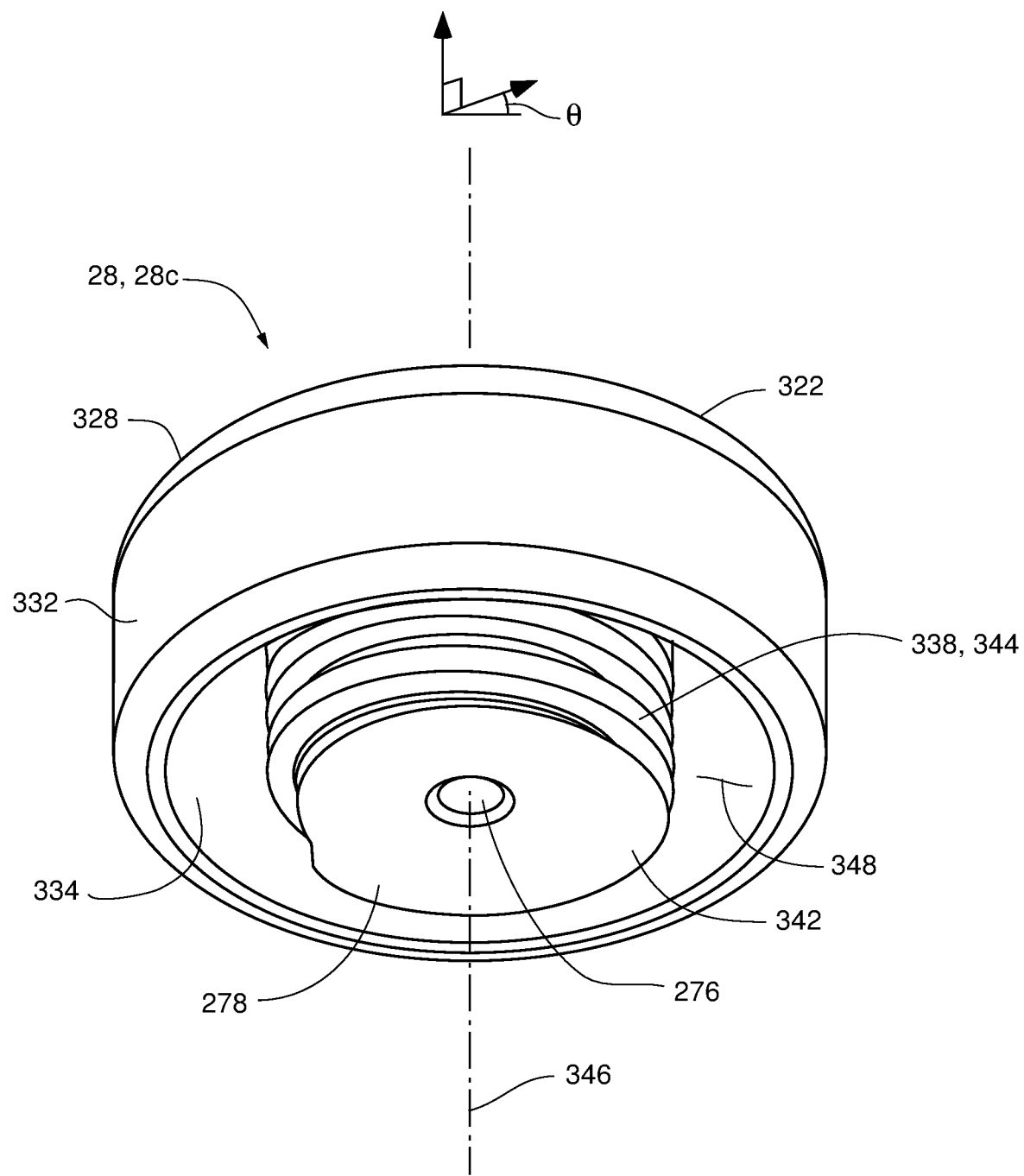
FIG. 7 is a lower perspective view of a reinforcement cap according to an embodiment of the disclosure.
Figure 8:
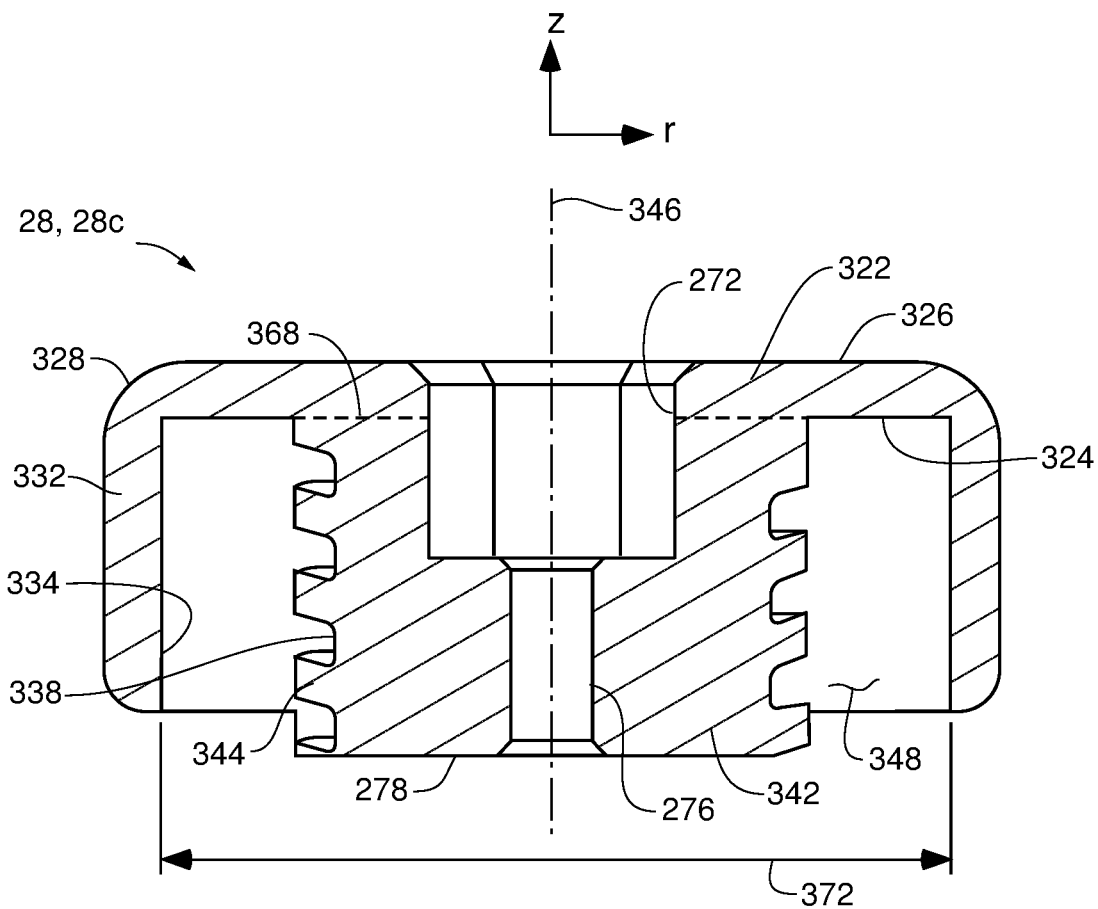
FIG. 8 is a sectional view of the reinforcement cap of FIG. 7 according to an embodiment of the disclosure.

Referring to FIGS. 7 and 8, a reinforcement cap 28c is depicted according to an embodiment of the disclosure. The reinforcement cap 28c includes many of the same components and attributes as the reinforcement cap 28a and 28b, which are indicated with same-numbered reference characters. A distinction of the reinforcement cap 28c is that the skirt portion 332 does not include interior threads, such that the skirt portion 332 slidingly engages and rotates about the exterior threads 96 of the base rod receptacle 24 but does not threadably engage the exterior threads 96. Accordingly, the reinforcement cap 28c threadably engages only with the interior threads 94 of the side wall 82. In some embodiments, the skirt portion 332 may define an inner diameter 372 that slides over the exterior threads 96 with a close, sliding fit.

Figure 9:
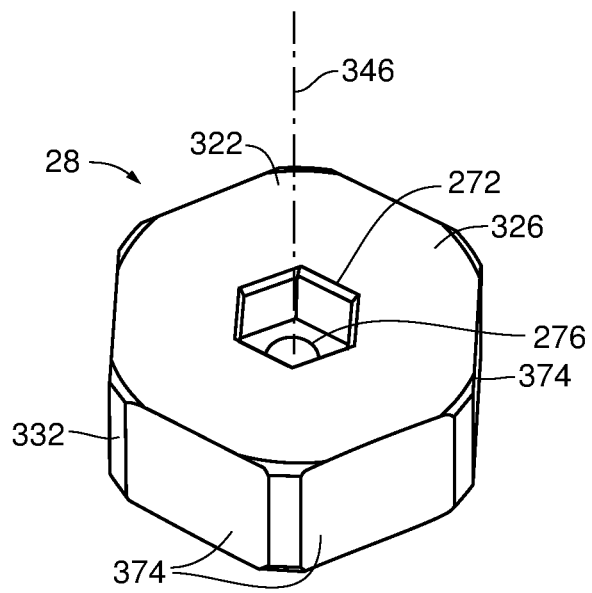
FIG. 9 is an upper perspective view of a reinforcement cap with flats according to an embodiment of the disclosure.

Referring to FIG. 9, the skirt portion 332 of the reinforcement cap 28 is depicted with flats 374 according to an embodiment of the disclosure. The flats 374 extend parallel to the rotation axis 346 and may be implemented with any of the depicted or contemplated reinforcement caps 28. The embodiment of FIG. 9 depicts a total of six flats 374 as a non-limiting example. In some embodiments the number of flats 374 is in a range of six to twelve inclusive. In some embodiments, the skirt portion 332 defines two flats 374 that are diametrically opposed. In some embodiments, the skirt portion 332 defines four flats 374 that are distributed as two diametrically opposed pairs that are rotationally offset at 90 degrees with respect to each other.

Functionally, the interior threads 94 of the spinal rod receptacle 24 are configured to mate with the exterior threads 344 of the set screw portion 342 of the reinforcement cap 28. For the reinforcement caps 28a and 28b, the exterior threads 96 of the spinal rod receptacle 24 are configured to mate with the interior threads 336 of the skirt portion 332 of the reinforcement cap 28, 28b. The socket 272 accommodates driving of the reinforcement cap 28, 28b with an appropriate mating wrench (e.g., hexagonal wrench for the depicted embodiment, or a square bit, rectangular bit, cross (PHILLIPS) bit, or star (TORX®) bit as appropriate). The flats 374, when implemented, provide an alternative way to apply torsion to the reinforcement cap 28, for example by use of socket tool that slides over and engages the flats 374. The flats 374 can also be used in so-called rescue situations, providing alternative gripping surfaces for removal of components of the spinal support system 20. The center passage 276 may be sized, for example, to accommodate sliding passage of a Kirschner wire or a guide rod.

The unitary structure of the set screw portion 342 with the platform portion 322 and skirt portion 344 provides additional structural strength and integrity relative to a separate cap and set screw arrangement. For example, the spinal support system 20 provides greater resistance to lateral forces because the set screw portions 342 is integrated with the platform portion 322, establishing a shear stress at a junction 368 of the screw portion 342 and the platform portion 322 that provides additional resistance to deformation relative to an assembly where the cap and set screw are separate components. The added strength and structural integrity provided by the integrated arrangement of the reinforcement cap 28 may be advantageous for high torque and high stress applications, such as scoliosis correction.

The tapped center hole 360 may function to facilitate mounting of an extension rod receptacle (not depicted). Arrangements for such extensible systems are disclosed at U.S. patent application Ser. No. 15/970,368, entitled "Extension Ready Spinal Support Systems", filed on even date and owned by the owner of the present application, the disclosure of which is hereby incorporated by reference herein in its entirety.

Referring to FIGS. 10, 10A, 11, and 11A, threads defining a canted cantilever profile 450 and the advantage provided over conventional threaded arrangements are depicted and described according to embodiments of the disclosure. A conventional threaded arrangement 400, schematically depicted at FIGS. 10 and 10A, may include, for example, exterior threads 402 of a set screw 404 that are engaged with interior threads 406 of a wall segment 408 of a spinal rod receptacle 410 (akin to opposed wall segments 90 of the spinal rod receptacle 24 of the spinal support system 20). Both the set screw 404 and the wall segment 408 are concentric about a central axis 412 that defines the z-axis of a right-cylindrical coordinate system 424 having an axial coordinate z and a radial coordinate r. When the set screw 404 is tightened in a first direction 416 to set against a spinal support rod 415, a clamping force vector FC is generated, for which there is the equal and opposite force vector FC' in a second direction 418 that is opposite the first direction 416. The force vector FC' in turn generates reaction force vectors FR generated at contact interfaces 422 between the exterior threads 402 of the set screw 404 and the interior threads 406 of the wall segment 408. The reaction forces FR generate an axial component FRZ and radial component FRR. Because of the standard shape of the threads 402 and 406, the radial components FRR generate a radial outward force FRO, i.e., away from the central axis 412.

For configurations such as the depicted spinal support system 20, the wall segment 408 (e.g., wall segment 90 of the spinal support system 20) is, in some embodiments, not supported by any additional structure. In such embodiments, the wall segment 408 will tend to cause deflections 6o that deflect radially outward in response to the radial outward force FRO. As the wall segment 408 deflects radially outward, the overlap between the threads 406 and 408 at the interfaces 422 is reduced, thereby weakening the coupling between the set screw 404 and the wall segment 408. The tighter the draw on the set screw 404, the greater the radial outward force FRO and the greater the deflection of the wall segment 408, further decreasing the overlap at the interfaces 422. Accordingly, as the torque requirements of the conventional set screw 404 are increased, the coupling between the set screw 404 and the wall segment 408 becomes more tenuous. Over time, creep stresses may cause the deflection of the wall segment 408 and the attendant decrease in the overlap at the interfaces 422, causing the clamping force FC to reduce. This can cause loosening of the assembly and slippage of the resident spinal rod within the spinal rod receptacle 410. In some instances, torque requirements can cause the set screw 404 to slip within the spinal rod receptacle 410 during implantation.

Figure 11:
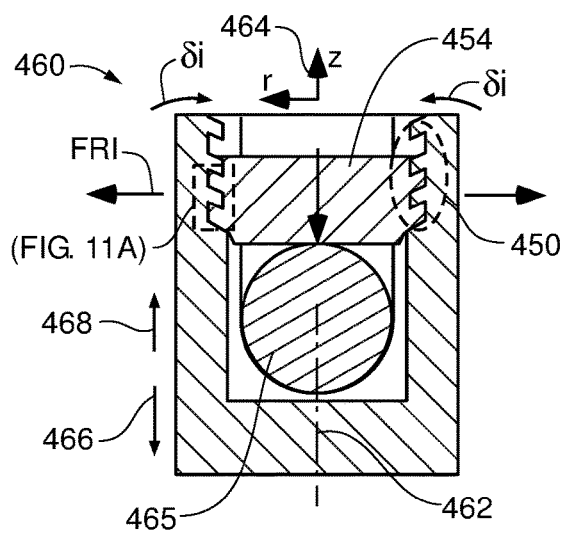
FIG. 11 is a sectional view of a rod receptacle in assembly having threads that define canted cantilever profile according to an embodiment of the disclosure.
Figure 11A:
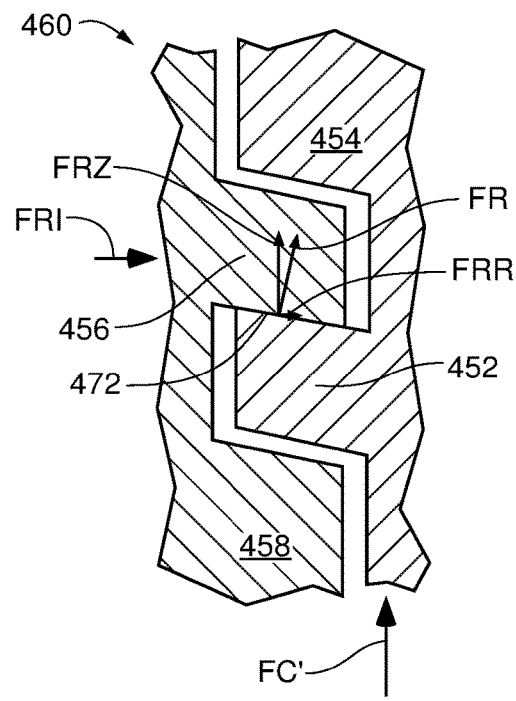
FIG. 11A is an enlarged, partial view of FIG. 11 according to an embodiment of the disclosure.

A threaded arrangement utilizing threads having the canted cantilever profile arrangement 450 is schematically depicted at FIGS. 11 and 11A. The various threads 94, 96, 336, 344, and 364 of the spinal support system 20 may utilize a canted cantilever profile arrangement. The canted cantilever profile arrangement 450, may include, for example, exterior threads 452 of a set screw 454 that are engaged with interior threads 456 of a wall segment 458 of a spinal rod receptacle 460 (akin to opposed wall segments 90 of the rod receptacle 24 of the spinal support system 20). Both the set screw 454 and the wall segment 458 are concentric about a central axis 462 that defines the z-axis of a right-cylindrical coordinate system 464 having an axial coordinate z and a radial coordinate r. When the set screw 454 is tightened a first direction 466 to set against a spinal support rod 465, the clamping force vector FC is generated, for which there is the equal and opposite force vector FC' in a second direction 468 that is opposite the first direction 466. The force vector FC' in turn generates reaction force vectors FR generated at contact interfaces 472 between the exterior threads 452 of the set screw 454 and the interior threads 456 of the wall segment 458. The reaction forces FR generate an axial component FRZ and radial component FRR.

However, unlike the conventional threaded arrangements 400, the contact interfaces 472 of the canted cantilever profiles 450 are sloped radially inward (i.e., toward the central axis 462) in the first direction 466. By this arrangement, the radial component FRR is vectored inward, toward the center axis 466. The forces so generated will tend to cause deflections 6i of the wall segment 458 that is radially inward in response to the radial inward force FRI. Because of the radial inward deflections 6i, the wall segments 458 tend to be supported by radial interference and friction with the set screw 454. Accordingly, the coupling between the set screw 454 and the spinal rod receptacle 460 provided by the canted cantilever profile arrangement 450 is stronger and can provide a greater clamping force FC than can the conventional threaded arrangement 400 of spinal rod receptacle 410.

For the spinal support system 20, the interior threads 94 of the rod receptacle 24 interact with the set screw portion 342 in the manner described attendant to the canted cantilever profile arrangement 450 of FIGS. 11 and 11A. The exterior threads 96 of the rod receptacle 24 may also implement a canted cantilever arrangement (see, e.g., FIG. 2), but may be configured to generate opposing forces and deflections. For example, the exterior threads 96 of the rod receptacle 24 are sloped radially outward (i.e., away the central axis 462) in the distal direction 74. By this arrangement, the radial components of the reaction forces at the interface of the exterior threads 96 and the interior threads 336 of the skirt portion 332 are vectored outward, away from the center axis 67. The forces so generated will tend to cause the wall segments 90 to deflect radially outward. Because of the radial outward deflections, the wall segments 90 tend to be supported by the skirt portion 332. The skirt portion 332, being tangentially continuous, incurs a hoop stress that counters the outward radial forces, thus limiting deflections and attendant stresses to the wall segments 90. The outward radial forces FRO at the exterior threads 96 also tend to counter and can be tailored to balance the inward radial forces FRI to further reduce overall radial deflection and deformation of the wall segments 90.

Figure 10:
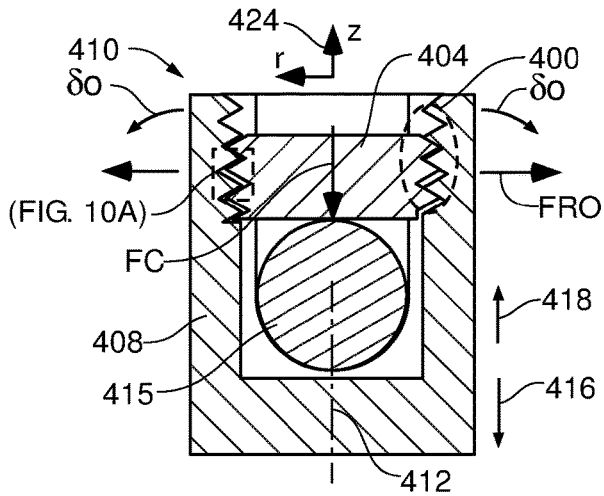
FIG. 10 is a sectional view of a conventional rod receptacle in assembly.
Figure 10A:
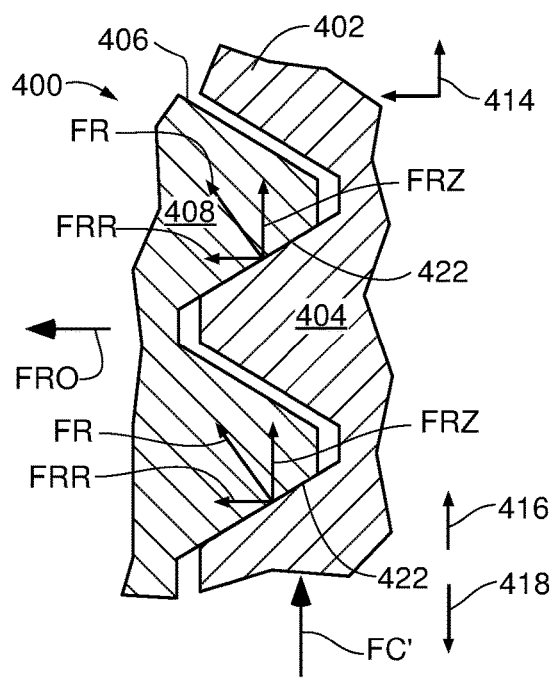
FIG. 10A is an enlarged, partial view of FIG. 10.

Alternatively, the exterior threads 96 of the spinal rod receptacle 24 and the interior threads 336 of the skirt portion 332 may be of a conventional arrangement. Conventional threads, as described attendant to FIGS. 10 and 10A, provide radial outward forces that are subsequently supported by the skirt portion 332 and as a counter to the radial inward force FRI.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A reinforcement cap for a spinal support system, comprising:
   a platform portion including a distal face and a proximal face separated by a perimeter portion;
   a skirt portion that extends from said distal face of said platform portion, the skirt portion including an interior surface, at least a portion of said interior surface including interior threads formed thereon; and
   a set screw portion that extends from said distal face of said platform portion, said set screw portion being surrounded by said skirt portion and including an exterior surface that faces radially outward, at least a portion of said exterior surface including exterior threads formed thereon, said set screw portion defining a rotation axis, said set screw portion and said skirt portion being concentric about said rotation axis to define an annular gap between said exterior threads of said set screw portion and said interior threads of said skirt portion,
   wherein said skirt portion and said set screw portion are integral to said platform portion, causing said set screw to be in a permanently fixed relationship with said skirt portion.

2. The reinforcement cap of claim 1, wherein said skirt portion includes an exterior surface that is tangential with said perimeter portion.

3. The reinforcement cap of claim 1, wherein said skirt portion includes an exterior surface that defines a plurality of flats, each of said plurality of flats being parallel to said rotation axis.

4. The reinforcement cap of claim 1, wherein said exterior threads of said set screw portion define a canted cantilever profile.

5. The reinforcement cap of claim 4, wherein said interior threads of said skirt portion define a canted cantilever profile.

6. The reinforcement cap of claim 4, wherein said canted cantilever profile of said set screw portion slopes in a distal direction and toward said rotation axis.

7. The reinforcement cap of claim 6, wherein said interior threads of said skirt portion define a canted cantilever profile.

8. The reinforcement cap of claim 6, wherein said canted cantilever profile of said skirt portion slopes in a distal direction and away from said rotation axis.

9. The reinforcement cap of claim 1, wherein said platform portion defines a socket accessible from said proximal face, said socket being concentric with and extending along said rotation axis.

10. The reinforcement cap of claim 9, wherein said platform portion defines a tapped center hole accessible from said proximal face, said tapped center hole being concentric with and extending along said rotation axis, said socket extending distally from said tapped center hole.

11. The reinforcement cap of claim 10, wherein said reinforcement cap defines a center passage concentric with said rotation axis and extending from said socket through a distal end of said set screw portion.

12. The reinforcement cap of claim 1, wherein said platform portion defines a tapped center hole accessible from said proximal face, said tapped center hole being concentric with and extending along said rotation axis.

13. The reinforcement cap of claim 1, wherein said set screw portion extends distally beyond said skirt portion.

14. The reinforcement cap of claim 1, wherein said skirt portion, said set screw portion, and said platform portion are unitary.

15. A spinal support system, comprising:
- a platform portion including a distal face and a proximal face separated by a perimeter portion;
- a skirt portion that extends from said distal face of said platform portion, the skirt portion including an interior surface, at least a portion of said interior surface including interior threads formed thereon;
- a set screw portion that extends from said distal face of said platform portion, said set screw portion being surrounded by said skirt portion and including an exterior surface that faces radially outward, at least a portion of said exterior surface including exterior threads formed thereon, said set screw portion defining a rotation axis, said set screw portion and said skirt portion being concentric about said rotation axis to define an annular gap between said exterior threads of said set screw portion and said interior threads of said skirt portion; and
- a spinal rod receptacle having a side wall that includes an interior surface and an exterior surface, the side wall defining a pair of diametrically opposed slots that extend axially along the side wall and are open at a proximal end of the spinal rod receptacle, the interior surface of the spinal rod receptacle defining interior threads, the exterior surface of the spinal rod receptacle defining first exterior threads, wherein said skirt portion and said set screw portion are integral to said platform portion, causing said set screw to be in a fixed relationship with said skirt portion, and wherein said interior threads of said spinal rod receptacle are configured to mate with said exterior threads of said set screw portion of said reinforcement cap, and said exterior threads of said spinal rod receptacle are configured to mate with said interior threads of said skirt portion of said reinforcement cap.

16. The spinal support system of claim 15, comprising a spinal rod configured for insertion into said diametrically opposed slots.

17. The spinal support system of claim 15, comprising a pedicle screw disposed within said spinal rod receptacle, a shaft of the pedicle screw extending distally from said spinal rod receptacle.

18. The reinforcement cap of claim 15, wherein said skirt portion, said set screw portion, and said platform portion are unitary.

\* \* \* \* \*